United States Patent
Mahdavi et al.

(10) Patent No.: US 6,468,414 B1
(45) Date of Patent: Oct. 22, 2002

(54) METHOD OF PURIFICATION OF A REDOX MEDIATOR BEFORE ELECTROLYTIC REGENERATION THEREOF

(75) Inventors: Behzad Mahdavi; Stephen Harrison; Kamyab Amouzegar, all of Shawinigan (CA)

(73) Assignee: Hydro-Quebec, Montreal (CA)

( * ) Notice: Subject to any disclaimer, the term of this patent is extended or adjusted under 35 U.S.C. 154(b) by 63 days.

(21) Appl. No.: 09/784,196

(22) Filed: Feb. 16, 2001

(51) Int. Cl.[7] ............................................. C02F 1/461
(52) U.S. Cl. ...................... 205/688; 205/742; 205/746; 205/751
(58) Field of Search ................. 205/688, 742, 205/746, 751

(56) References Cited

U.S. PATENT DOCUMENTS

| | | | |
|---|---|---|---|
| 2,450,858 A | 10/1948 | Fitzpatrick et al. | 260/406 |
| 2,813,113 A | 11/1957 | Goebel et al. | 260/406 |
| 3,423,300 A | 1/1969 | Joo et al. | 204/89 |
| 3,595,765 A | 7/1971 | Joo et al. | 204/89 |
| 3,682,796 A | 8/1972 | Dev Bedi et al. | 204/97 |
| 3,953,305 A | 4/1976 | Connolly | 204/97 |
| 4,006,067 A | 2/1977 | Gussack | 204/149 |
| 4,061,546 A | 12/1977 | Singleton | 203/31 |
| 4,118,295 A | 10/1978 | Korenowski et al. | 204/151 |
| 4,144,145 A | 3/1979 | Watanabe et al. | 204/89 |
| 4,273,628 A | 6/1981 | Kidon et al. | 204/87 |
| 4,337,129 A | 6/1982 | Soboroff et al. | 204/151 |
| 4,639,298 A | 1/1987 | Kreh et al. | 204/59 |
| 4,752,364 A * | 6/1988 | Dhooge | 205/746 |
| 4,857,162 A | 8/1989 | Phillips et al. | 204/257 |
| 4,859,294 A | 8/1989 | Vytlacil | 204/97 |
| 4,874,485 A * | 10/1989 | Steele | 205/698 |
| 5,045,162 A | 9/1991 | Herbst et al. | 204/130 |
| 5,296,107 A | 3/1994 | Harrison | 204/59 |
| 5,391,266 A | 2/1995 | Stenzel et al. | 204/89 |
| 5,855,763 A * | 1/1999 | Conlin et al. | 205/742 |
| 6,402,932 B1 * | 6/2002 | Bremer et al. | 205/701 |

FOREIGN PATENT DOCUMENTS

| | | |
|---|---|---|
| EP | 0 075 828 | 4/1983 |
| WO | WO 86/05215 | 9/1986 |

OTHER PUBLICATIONS

Harrison, et al, *The Electrosysthesis of Naphthoquinone and Tetrahydroanthraquinone*, J. New Mat. Electrochem. Systems 2, 1–9 (1999). Jan.

* cited by examiner

Primary Examiner—Arun S. Phasge
(74) Attorney, Agent, or Firm—Foley & Lardner (57) ABSTRACT

A method for purifying a Redox mediator used in a chemical process of oxidation of organic compounds. The desired purification is obtained by recovering the mediator in the form of a solution and heating this solution to evaporate the volatile impurities contained in it and to oxidize the non volatile impurities into compounds which precipitate and are extracted by filtration. The purification takes place before the mediator is regenerated in the electrolysis cell. This prevents the impurities contained in the mediator solution to negatively affect the operation of this cell.

20 Claims, 7 Drawing Sheets

METHOD OF PURIFICATION OF A REDOX MEDIATOR BEFORE ELECTROLYTIC REGENERATION THEREOF

FIELD OF THE INVENTION

The invention relates to a method for purifying a Redox mediator before electrolytic regeneration thereof during a chemical oxidation process of organic compounds.

DESCRIPTION OF PRIOR ART

It is well known that oxidation of unsaturated long chain fatty acids such as oleic acid, yields short chain fatty diacids, such as azelaic acid or pelargonic acid. Usually, such an oxidation is carried out with a solution of chromic (Cr VI) acid and sulfuric acid produced by electrolysis of an aqueous solution of chromium (Cr III) sulphate and sulfuric acid. During the electrolysis, hydrogen is released at the cathode and the chromium sulfate is converted into chromic acid and sulfuric acid at the anode (see U.S. Pat. No. 2,450,858 granted in 1948).

When this type of oxidation (also called indirect electrosynthesis) is used, it is customary to recover the solution of chromium sulfate and sulfuric acid obtained after the oxidation reaction. The so-recovered solution is then recycled towards an electrolysis cell in order to regenerate it to obtain the desired ionic species for the oxidation reaction.

A major difficulty of this process of recovering and regeneration of the electrolyte lies in the presence of organic impurities in the electrolytic solution. It turns out that these impurities accumulate and deposit on the electrodes of the electrolysis cell. This results in a reduction of the electrolysis current efficiency.

It is also known that solutions of Cerium III/Cerium IV are used for the electrochemical oxidation of other types of organic products. Electrochemical oxidation of other types of organic products such as, but not limited to aromatic aldehydes and quinones as described by HARRISON in U.S. Pat. No. 5,296,107 and by KREH et al in U.S. Pat. Nos.: 4,639,298; 4,647,349; 4,620,108; 4,701,245 and 4,794,172. The commercial applicability has been described by HARRISON in Journal of new Materials for Electrochemical Systems, January 1999.

Work done by the LTEE in collaboration with W. R. Grace & Co. has led to the development of a generic technology for the selective manufacture of a whole array of chemical products of high interest. The success of this technology has already been confirmed during pilot projects directed to the synthesis of anthraquinone, aminoanthraquinone and para-tolualdehyde.

However, even in these cases, the presence of soluble organic compounds in the mediator solution recovered at the end of the reaction considerably affects the regeneration efficiency of the catalyst in an electrolytic cell. More precisely, these compounds affect the current efficiency and the lifetime of the electrodes and they generate drawbacks of operation in continuous mode. It turns out that the presence of organic compounds can block the surfaces of the electrodes and therefore reduce the production rate of the Redox mediator. To maintain this rate, the current must be increased.

In light of the above, it is therefore obvious that it is essential to purify the electrolytic solution recovered after the oxidation reaction before regenerating it.

In order to do it, it has already been suggested to treat the mediator solution with activated charcoal to absorb the dissolved organic molecules present in it. Although this method seems to work, it has a number of drawbacks.

First of all, it is costly because the consumption of activated charcoal expressed in kg per kg of obtained product is high (this is a direct consequence of the low electrolyte concentration and therefore of the high $V_{electrolyte}/kg_{product}$ ratio).

Secondly, after use, the activated charcoal must either be discarded or regenerated, but before doing so, the redox mediator must be recovered for economic and environmental reasons. Such can be done by washing the activated charcoal with water. However, concentrating the recovered redox reagent by evaporation is energy intensive. Handling of wet activated charcoal is also a labour intensive activity (this is a time consuming operation that results in higher labor costs and production costs).

Thirdly, this method cannot be used on non organic molecules and non-aromatic products having a low affinity for activated charcoal.

SUMMARY OF THE INVENTION

The object of the invention is to solve the above-mentioned problem that occurs in all the chemical processes that use electrochemically regenerated Redox couples.

More precisely, the object of the present invention is to provide a method that is both simple and efficient to solve the problem that was previously mentioned. This method essentially consists of purifying the solution containing the Redox mediator that is recovered from the oxidation reactor before introducing it into the electrolysis cell where the regeneration takes place. This purifying step is of a great importance since it allows removal of organic impurities that tend to deposit on the electrodes or consume regenerated mediator if they are not extracted from the electrolytic solution and which can therefore affect the operation of the electrolysis cell and the efficiency of the regeneration.

Thus, the method according to the invention is devised to purify a Redox mediator used in a chemical oxidation process of organic compounds before this mediator is regenerated electrochemically in an electrolysis cell. This method comprises the steps of:

recovering the mediator in the form of a solution containing volatile, soluble and insoluble impurities;

subjecting the solution containing the mediator to a thermal treatment, this thermal treatment being carried out in a reactor kept at a temperature high enough to allow oxidation of the impurities by means of left-over unused mediator that is still present in the solution under its oxidative form, or by addition of a given amount of said regenerated mediator and simultaneously to allow elimination of the volatile impurities present in the solution; and filtering the solution that contains the mediator, to remove the insoluble impurities therefrom.

This series of steps constitutes the heart of the invention since it considerably increases the technical and economical feasability of the whole chemical process.

In this connection, it is worth mentioning that this method for purifying an electrolyte, is generic, economical and compatible with all the processes used for the treatment of an electrolyte in view of efficiently recycling it.

DETAILED DESCRIPTION OF THE INVENTION

As previously mentioned, the method according to the invention is intended to be used for purifying a Redox mediator before regenerating it in an electrolysis cell.

As non-restrictive examples of Redox mediators, reference can be made to Ce III/Ce IV mediator, Cr IV/Cr IV mediator and a mixture thereof.

The Ce III/Ce IV mediator can be used in the following process for the synthesis of:
  p-tolualdehyde starting from p-xylene;
  naphtoquinone and its derivatives starting from naphtalene and its derivatives; or
  chlorobenzoquinone starting from chloroaniline.

The Cr III/Cr IV mediator or a mixture of Ce III/Ce IV and Cr III/Cr IV can be used for the synthesis of azelaic and pelargonic acids starting from oleic acid.

The above mentioned examples of processes are given for illustrative purposes only. In fact, there are numerous other Redox couples with similar possible uses.

The first step of the method according to the invention is conventional and is presently already in use. It consists of recovering the electrolytic mediator to be regenerated in the form of a solution. Coming out of the reactor, this solution usually contains volatile, soluble and insoluble impurities along with the catalyst, a small amount of which is still active.

The second step consists in subjecting the recovered solution to a thermal treatment. This treatment is carried out in a reactor that is kept at a temperature that is high enough to allow oxidation of the impurities by means of the left-over unused mediator that is almost always present in the solution. This thermal treatment also permits to eliminate volatile impurities. In pratice, in the case of the above-mentioned processes listed as examples, the reactor can be kept at a temperature ranging between 40 and 120° C., preferably 70 and 110° C., and more preferably between 90 and 100° C.

The third and last step consists of filtering the solution in order to remove the insoluble impurities contained therein, before it is fed to the electrolysis cell.

Figure 1:
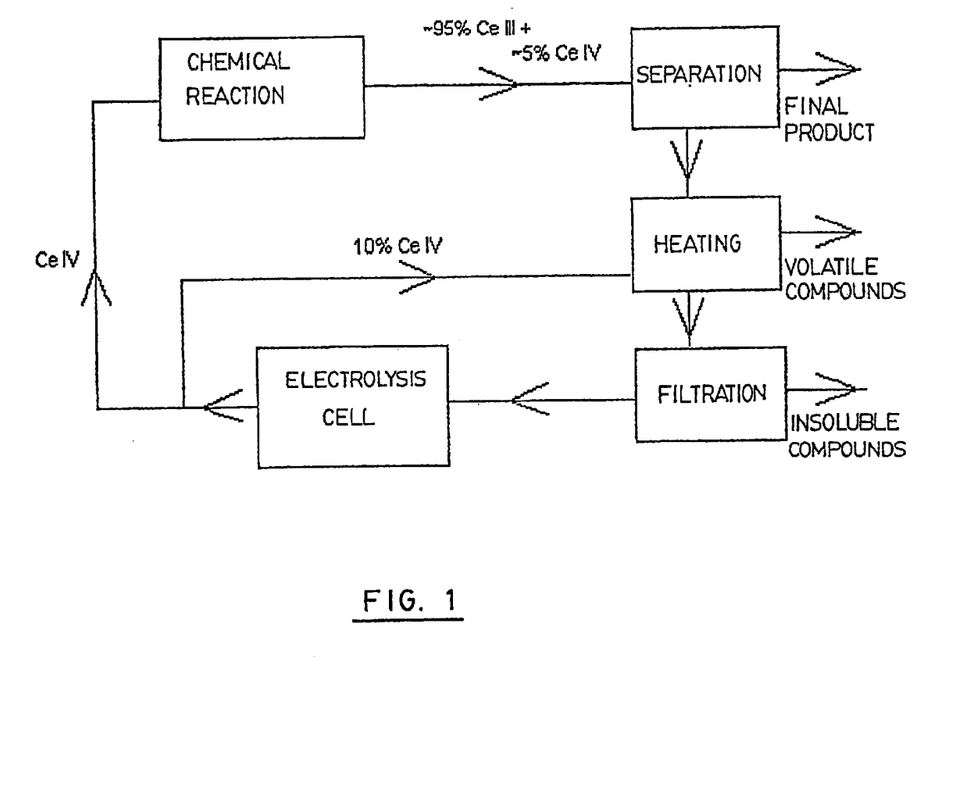
FIG. 1 is a schematic diagram of a process for the chemical oxidation of organic compounds which incorporates the method according to the invention.
Figure 2:
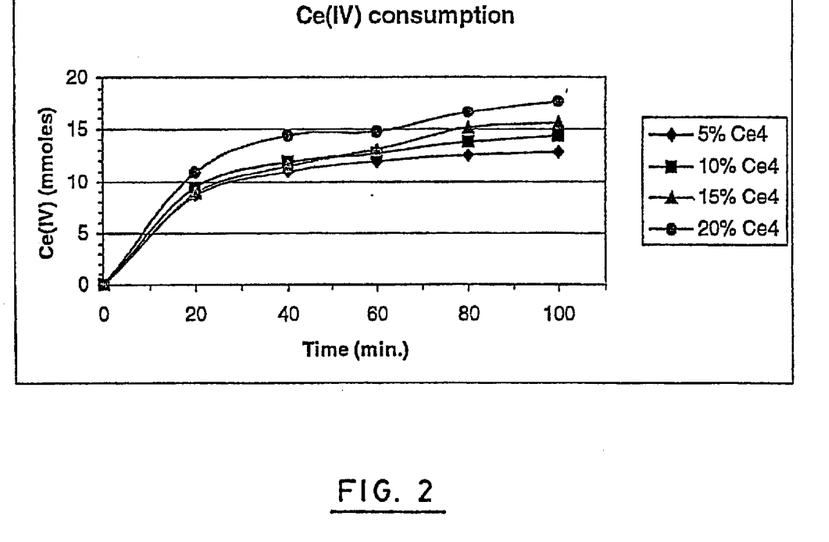
FIG. 2 is a graph showing the Ce IV consumption in the reactor used for the thermal treatment, as a function of the time and of different excess quantities of Ce IV added at a 60° C. temperature during 100 minutes when the method of purification according to the invention is used in a process for the oxidation of p-xylene to p-tolualdehyde.
Figure 3:
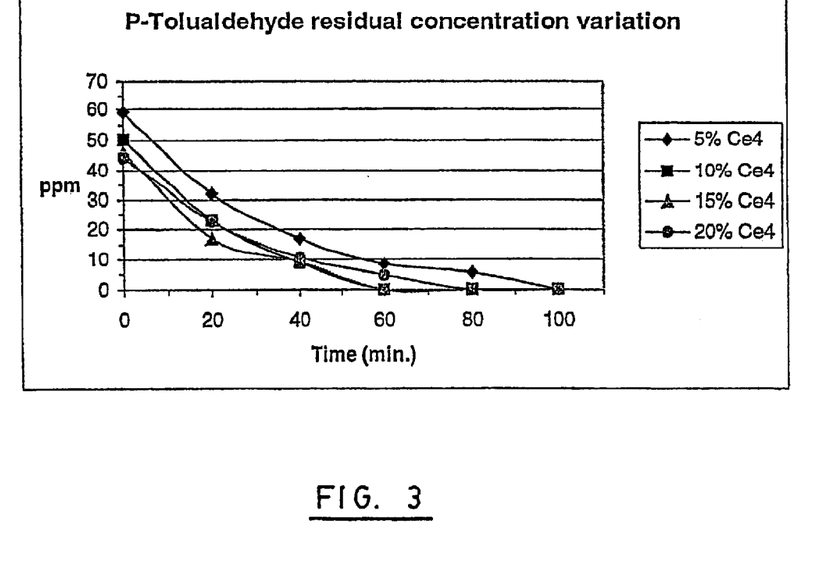
FIG. 3 is a graph showing the amount of p-tolualdehyde in the reactor as a function of the time and of different excess quantities of Ce IV added under the same conditions as in FIG. 2.
Figure 4:
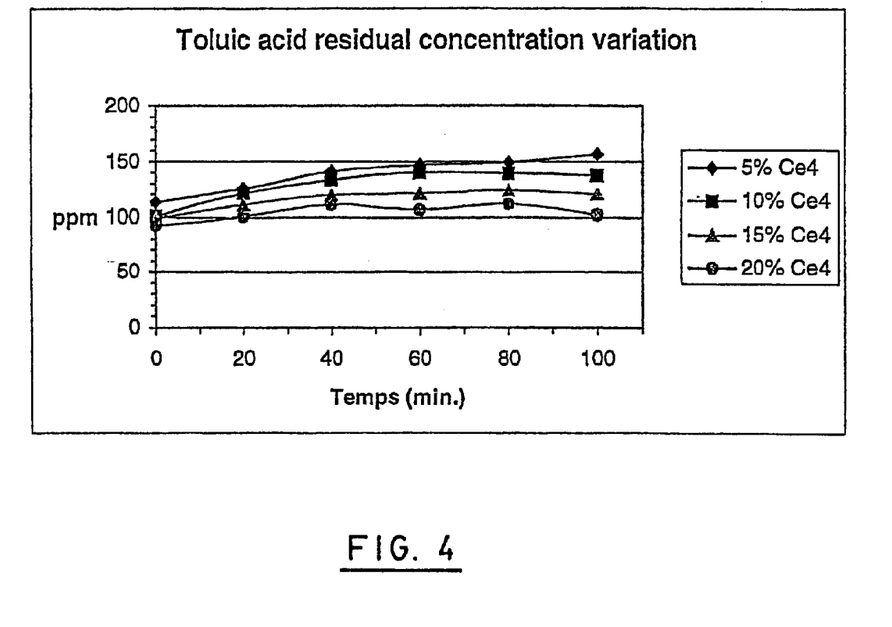
FIG. 4 is a graph showing the amount of toluic acid in the reactor as a function of the time and of different concentrations of Ce IV added under the same conditions as in FIG. 2.
Figure 5:
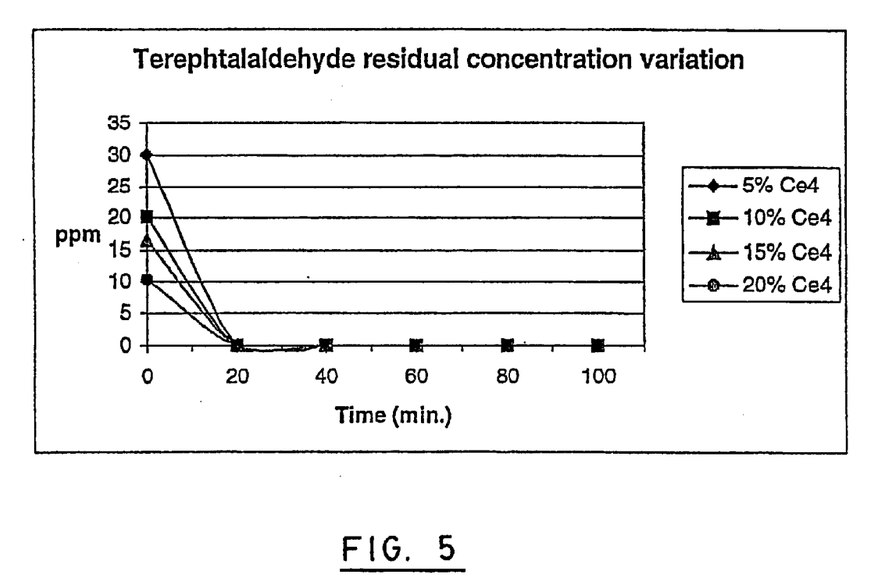
FIG. 5 is a graph showing the amount of terephtaldehyde in the reactor as a function of the time and of different concentrations of Ce IV added under the same conditions as in FIG. 2.
Figure 6:
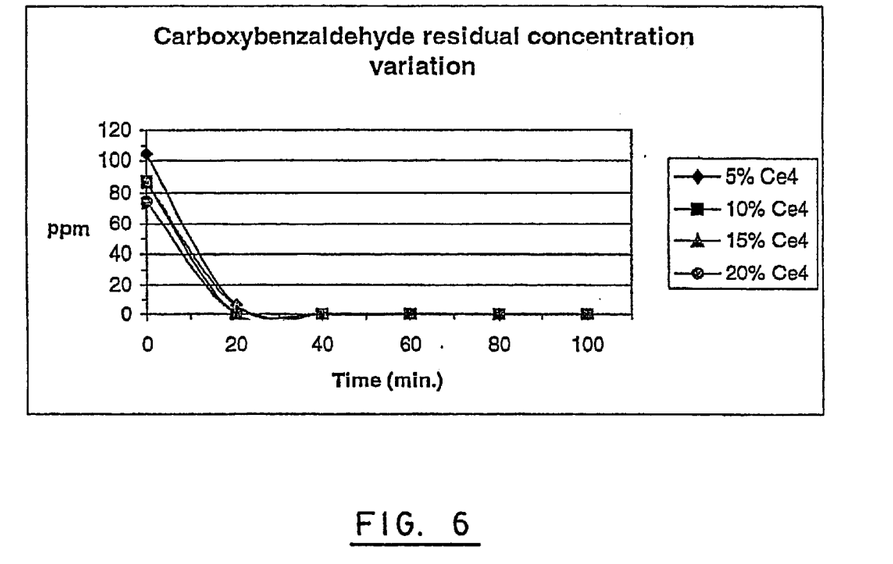
FIG. 6 is a graph showing the amount of carboxybenzaldehyde in the reactor as a function of the time and of different concentrations of Ce IV added under the same conditions as in FIG. 2.
Figure 7:
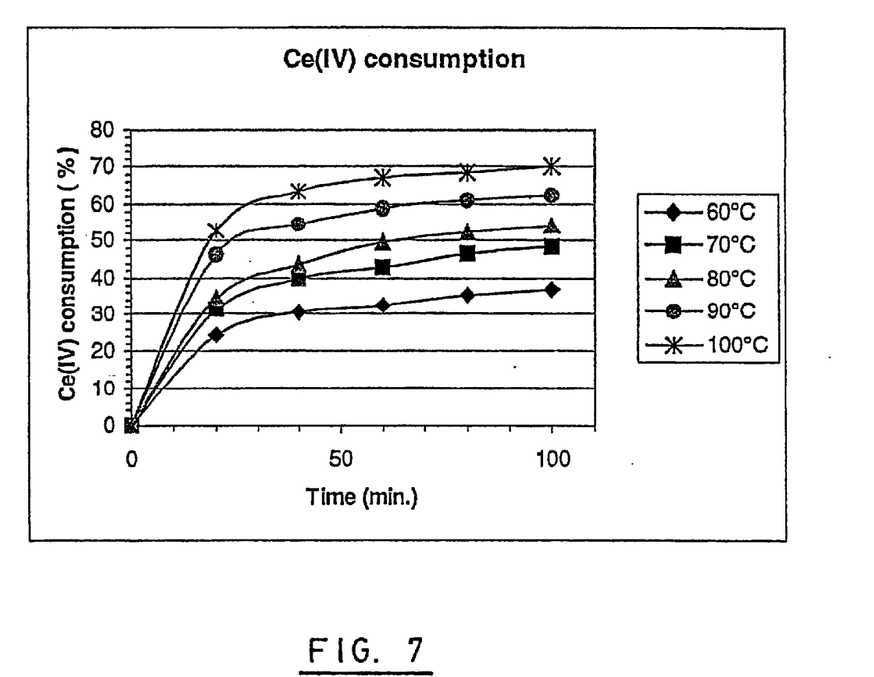
FIG. 7 is a graph showing the Ce IV consumption (in %) in the reactor as a function of the time, with an excess quantity of added Ce IV of 10% and at different temperatures for 100 minutes, when use is made of the purifying method according to the invention.
Figure 8:
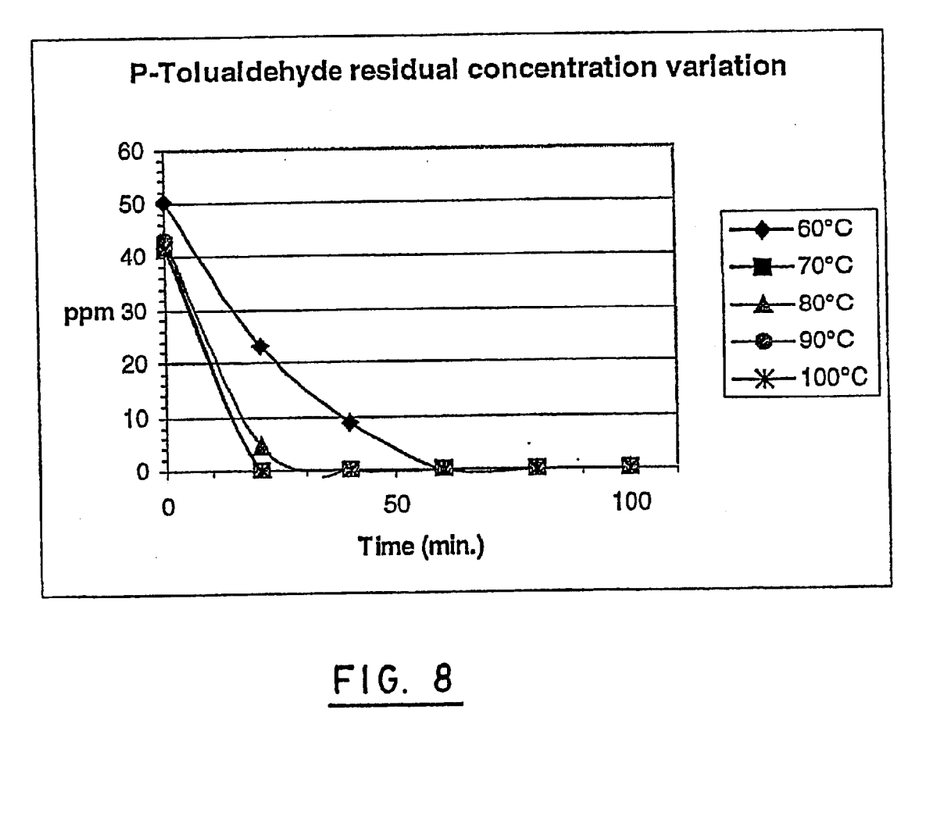
FIG. 8 is a graph showing the amount of p-tolualdehyde in the reactor as a function of the time under the same conditions as in FIG. 7.
Figure 9:
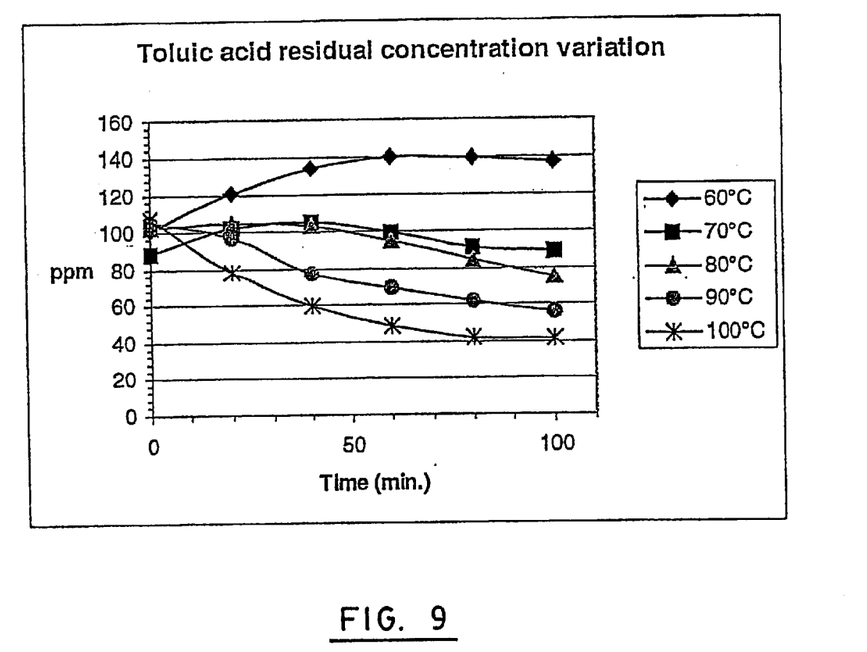
FIG. 9 is a graph showing the amount of toluic acid in the reactor as a function of the time under the same conditions as in FIG. 7.
Figure 10:
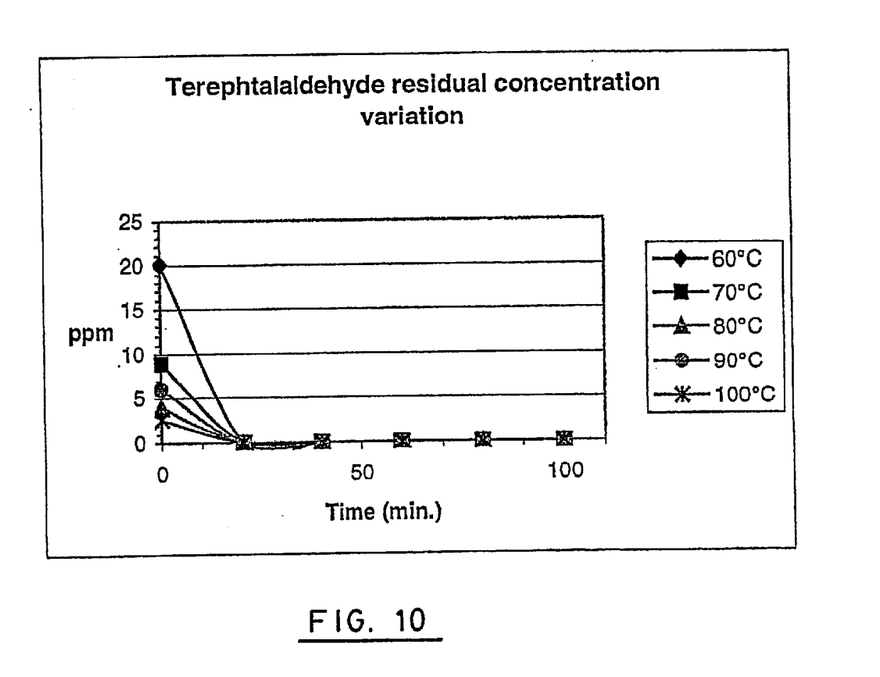
FIG. 10 is a graph showing the amount of terephtaldehyde in the reactor as a function of the time under the same conditions as in FIG. 7.

In the event that the left-over unused oxidation mediator present in the recovered solution is insufficient to obtain the desired treatment it is possible to add to the solution a given amount of the mediator regenerated in the electrolysis cell, as illustrated in FIG. 1. Therefore, for example, in the case illustrated in FIG. 1, 10% of the regenerated mediator (Ce IV) is added to the solution in order to increase the amount of active mediator (Ce IV) present in the recovered solution, which in this case is only 5%. Of course, the amount of regenerated mediator to be added may substantially vary, since it depends on the parameters of the chemical reaction and of the required need for an oxidizing agent, to eliminate the impurities present in the solution.

As can be understood, the method according to the invention allows for maximum oxidation of the organic by-products present in the electrolyte. As aforesaid, this oxidative step is carried out at high temperature in the presence of the leftover mediator and/or of regenerated mediator added to the solution.

In practice, the method according to the invention has several advantages.

First of all, the organic molecules become inert, under their most oxidized form and they can no longer react with the electrolyte that is produced in the electrolysis cell. Control on the current efficiency can therefore be obtained more easily.

Secondly, oxidation of most of the organic molecules results in the formation of organic acids. These organic acids have very low solubilities and precipitate as solids. The subsequent filtration that is preferably tangential, permits to extract these acids from the electrolytic medium and therefore to lower the organic load of the electrolyte. Therefore, the lifetime of the electrodes is less affected due to the fact that the electrolyte is purer.

Thirdly, the high temperature permits to evaporate any residual solvent as well as all the volatile organic molecules without even having to subject them to an oxidation. The so evaporated leftover solvent can be recycled in the process.

Fourthly, this method which actually amounts to a <<stabilization>> by oxidation of the recovered solution, can be applied to all aromatic and aliphatic organic molecules.

Thus, the method according to the invention has the advantages of being generic, effective and functional for the treatment of the electrolytes used in chemical processes of oxidation also known as "indirect electrosynthesis". The thermal treatment of the used electrolyte is the key feature of the method according to the invention. This thermal treatment is simple and very advantageous since it does not require any additional equipment. In fact, it only requires an increase in the capacity of the electrochemical cell.

As previously mentioned, one can add a given amount of mediator regenerated in the electrolysis cell directly to the reactor where the purification takes place to help completion of the oxidation of the solution containing the mediator and the impurities. In other words, part of the regenerated electrolytic solution can be used solely for the oxidation of the used mediator solution.

It is important to mention that, during tests carried out by the Applicant, the method according to the invention was only subjected to one recycling. However, it could be expected that a greater number of recycling, for example or more, would help to increase the efficiency of the treatment and verify that the efficiency of the regeneration current and the amount of residual organic products in the electrolyte, stabilize after a given number of recyclings.

The following examples illustrate the invention. These examples are non-restrictive and given only for informative purposes.

EXAMPLE 1

Application of the Method According to the Invention in a Process of Synthesis of p-tolualdehyde

It is known that the synthesis of p-tolualdehyde is carried out by oxidation of p-xylene in the presence of Ce (IV) that can be regenerated electrochemically at the anode of an electrolysis cell (see reaction 1 below). In that process, the starting material, viz. p-xylene, is oxidized with cerium (IV) in a chemical reactor under stirring to the corresponding aldehyde, p-tolualdehyde (PTA).

$$Ce(CH_3SO_3)_3 + CH_3SO_3H \rightarrow Ce(CH_3SO_3)_4 + H^+ + e^- \qquad (1)$$

By-products are also produced during this synthesis. The by-products result from an under-oxidation or over-oxidation of PTA (alcohols, acids, . . . ).

-continued terephtalic acid

After the chemical reaction is completed, the organic molecules listed above are present at different concentrations in the recovered solution containing the electrolyte. During the tests carried out by the Applicant, chemical yields of 85–90% of PTA were obtained. The major by-products were p-toluïc acid (10–14%) and terephtalic acid (1–2%). A large amount of the p-toluic acid can be removed by filtration after the chemical reaction. However, tests carried out in a pilot plant have shown that the p-toluïc acid represents approximately 5% of the formed products and therefore that the amount of p-toluïc acid in precipitated form is practically negligible. Three (3) consecutive extractions with cyclohexane helped to eliminate 80% of the p-toluïc acid in the acidic phase (residual concentration of 130 ppm). The residual concentration of said acid in the anolyte reservoir (70–80 ppm) was significantly reduced after treatment of the acidic phase with an activated charcoal (10 ppm, trial).

If the electrolyte is not purified, the above-mentioned molecules will react either at the electrode where the electrolyte is regenerated, or with the Ce IV regenerated at that electrode. These reactions will then generate a decrease in current efficiency. In the case where the by-products may adsorb on the surfaces of the electrodes, a current drop (or a voltage increase in galvanostatic mode) can be observed. This phenomenon is due to a decrease of the active surfaces of the electrodes. In this case, cleaning of the electrodes is necessary. In some cases, the presence of organic molecules can even affect the life span of the electrodes. For example, the life span of lead electrodes can be severely affected in the presence of acetic acid produced by oxydation of organic molecules.

The method according to the invention permits to <<stabilize>> these molecules by oxidation at high temperature in the presence of an excess of oxidant. This method allows a better control on the operation parameters (intensity, current efficiency). Moreover, it permits in some cases, to extract from the medium, a greater amount of the organic load by filtration. Preferably, a tangential filtration will be used in order to extract the solid organic particles in suspension in the solution. Such a use is important, since the solid particles to be extracted are usually of colloidal size and may clog the pores of conventional filters.

Thermal treatment produces highly oxidized molecules which are solid for the most part. Since these products are insoluble in the aqueous acid phase, they precipitate in the form of very fine particles that can be separated from the solution by tangential filtration.

This control on the operation parameters is extremely important and constitutes one of the most notable advantages of the method of purification according to the invention. The organic molecules react in a forced and rapid manner (due to the elevated temperature) outside of the electrochemical cell with the oxidized contaminants being separated before affecting electrode performance instead of reacting inside the electrochemical cell and affecting the electrode performance causing an uncontrollable drop in current efficiency (due to the consumption of regenerated mediator and the formation of deposits on the electrode surface).

During the tests carried out by the inventors, the following equipments were used:

Testing Bench:
  equipped glass chemical reactors of 20l and 2l
  Ce electrochemical cells with 40l and 2l capacity Chemical Analysis Apparatus:
  automatic titrators,
  CPV and HPLC. chromatographs for sample analysis.

The anolyte used in the tests consisted of a solution that was purified over actived charcoal. It was not a contaminated solution. To carry out the chemical reaction of oxidation, 50 liters of this solution were used with a concentration of 0,4 M of Ce IV. Table 1 characterizes the <<clean>> solution obtained before and after regeneration.

TABLE 1

Characterization of the cerium solution considered as "clean" (reference solution)

|  | Before regeneration | After Regeneration |
| --- | --- | --- |
| Ce (IV) (M) | 0,004 | 0,436 |
| Total Ce (M) | 0,746 | 0,723 |
| Acidity AMS (M) | 4,22 | 4,38 |
| Benzenedimethanol (ppm) | ND | ND |
| Terephtalic acid (ppm) | ND | ND |
| Carboxybenzaldehyde (ppm) | ND | ND |
| Terephtaldehyde (ppm) | ND | ND |
| 4-methylbenzylalcohol (ppm) | ND | ND |
| Toluic Acid (ppm) | ND | ND |
| PTA (ppm) | ND | ND |
| p-Xylene (ppm) | ND | ND |
| Unknown 3.85 min (ppm) | ND | ND |
| Unknown 7.32 min (ppm) | ND | ND |

Reaction

The synthesis reaction was carried out with equipment made up primarily of glass, stainless steel and Teflon®. As previously indicated, the equipment was composed of a 20l reactor with a thermocouple, a reflux condenser and a mixer. The oxidative solution had a concentration of Ce IV of about 0,4 M and a total cerium concentration of about 0,75 M. This solution was acidified with about 4 M in methanesulfonic acid ($CH_3SO_3H$). During the tests 16 I of this solution were necessary to carry out the reaction. The volume of reactant (solution to be oxidized) was determined as a function of the Ce IV concentration in the oxidative solution.

The reactant was added to the oxidative solution at a temperature of 60° C. The reaction was carried out under stirring with a mechanical stirrer for a predetermined time. The temperature was continuously monitored. At the end of the reaction, the stirring was stopped and the extraction step was perfomed as rapidly as possible.

The parameters of operation were the following:
  T=60° C.,
  Reaction time=10 min,
  Molar ratio (Ce IV/p-xylene)=4.5/1,
  Electrolyte acidity=4.5 MSA,
  Ce (total)=0,75 M and Ce IV=0,4 M.

After the chemical reaction, two consecutive extractions were carried out with p-xylene (starting material) at ambiant temperature.

The used electrolyte recovered in this way will hereafter be called the <<contaminated>> solution.

The contaminated solution having a lower amount of active cerium obtained after the reaction was then regenerated in an electrolysis cell. The set-up used in this case was the electrolysis set-up of Electrocatalytic Ltd., modified to fit a FM01-LC cell of ICI. This equipment is designed to resist acids (the piping is mostly composed of PVDF and Teflon®).

The contaminated solution containing mainly Ce III and methanesulfonic acid ($CH_3SO_3H$) was brought to the anodic compartment of the cell by a system of pumps and piping. In the anodic compartment, an electric current transformed Ce III into Ce IV up to a concentration of approximately 0.4 M. The electrolysis of the solution was done at 60° C.

By "cumulative efficiency of a solution", it is meant the capacity (in percentage) of a solution to transmit the current that is applied to it in order to carry out a desired reaction. In other words, the cumulative efficiency is the ratio of the current used to carry out the desired reaction to the applied current. In this example, the efficiency of the clean solution with a concentration of approximately 0.4 M of Ce IV, was of 92%. This efficiency was considered as the reference efficiency for the non contaminated or "clean" solution in this example. The efficiency of the thermal treatment of the electrolyte was therefore compared with a value of 92%, as will be seen hereafter.

Regeneration of the contaminated solution obtained with no treatment before its introduction into the electrolysis cell gave a new solution having the lowest current efficiency value that can be obtained for an anolyte that has only undergone one cycle in the system. This value is considered as the lowest one since no treatment was carried out on the electrolyte. The value obtained for the final current efficiency was 85%.

Thus, it appears that the presence of residual organic products in the electrolyte after one cycle of chemical reaction decreases the current efficiency by 5–7%. The purpose of the electrolyte treatment carried out by the method according to the invention is to increase this efficiency to get a current efficiency close to the one of the "clean" solution.

Optimization of the Treatment

In the thermal treatment, three factors are extremely important: the duration of of treatment, the temperature of treatment and the concentration of Ce (IV) in the recovered solution.

The latter factor, viz. the Ce (IV) concentration, must be minimized. Indeed, the amount of Ce (IV) solution to be added to the medium in order to carry out the oxidation of the impurities is proportional to the energetic consumption of the cell. The larger is the added amount of Ce (IV), the higher are the energy costs for the treatment. Moreover, the impact is not only on the operation costs but also on the capital costs because additional electrochemical cells may be necessary.

The advantage of the purification method according to the invention lies in its simplicity because it does not require any additional equipment. It only requires enlargement of the existing equipment.

It should be noted that during the treatment, the residual Ce(IV) is lost due to the fact that activated charcoal column could still be used in the process for safety reasons and the fact that Ce (IV) reacts with activated charcoal.

Thus, it is essential to determine the minimum quantity of Ce (IV) that must be added to the used electrolyte to carry out the oxidation of the impurities.

The duration and temperature of treatment must also be selected to have a short and efficient time of treatment. Proper temperature selection permits to decrease the duration of treatment and to oxidize some organic molecules that can not be oxidized at lower temperatures.

The thermal treatment was optimized in the case of p-tolualdehyde with these three variable parameters: duration of treatment, temperature and amount of Ce (IV).

Ce (IV) Concentration (Lower Limit)

The object of this section consists of evaluating the minimum quantity of Ce (IV) to be added to the used electrolyte in order to fully oxidize the residual organic products present in it. To find this lower limit, the above-mentioned chemical reaction was carried out under the conditions described previously.

After completion of the chemical reaction, two consecutive extractions were carried out to extract the products of the reaction from the electrolyte. The obtained electrolyte was used as reference and is hereinafter called the "contaminated and untreated electrolyte". To this contaminated electrolyte, 5%, 10%, 15% and 20% in volume of the initial electrolyte having a concentration of about 0,4 M of Ce (IV) were added during the tests. Then, these solutions were heated under stirring at T=60° C. for 100 minutes. This allows to determine the minimal quantity of Ce (IV) necessary to carry out the desired extensive oxidation.

The amount of cerium as well as the amount of the reaction products in the solution were measured as a function of the time and the results are reported in FIGS. 2 to 6. Table 2 shows the residual amount of Ce IV as a function of the added amount of Ce IV.

TABLE 2

Concentration of Ce (IV) as a function of the amount of Ce (IV) added initially

| Ce (IV) added initially | 5% | 10% | 15% | 20% |
|---|---|---|---|---|
| Ce (IV) added (mmoles) | 18.48 | 39.09 | 60.24 | 82.87 |
| Residual Ce (IV) (mmoles) | 5.64 | 24.67 | 44.68 | 65.14 |
| Residual Ce (IV) (%) | 30.5 | 63.1 | 74.7 | 78.6 |

FIGS. 2 to 6 illustrate the performance of the different amounts of Ce IV used in the tests in relation to the different chemical products found in the electrolyte solution stemming from the oxidation process of p-tolualdehyde.

Based on the results that were so obtained, an addition of 10% would be a good compromise. This amount permits to leave a surplus of cerium as a precautionary measure.

Effect of the Temperature and Duration of Treatment

The next step was to optimize the temperature and the duration of treatment. Obviously, these two parameters are linked, and theoretically, the higher is the temperature, the shorter should be the reaction time. The object of this step was to find an interesting compromise between the temperature of treatment and the duration of the treatment. The treatment time is a critical factor for carrying out the process in a continuous mode since a long reaction time results in a higher volume of electrolyte in circulation and the need for larger reactors.

Tests were carried out at different temperatures. A sampling was performed at precise intervals to determine the best duration for this type of treatment in the case of the electrosynthesis of PTA. The tests were carried out with the addition of 10% of Ce IV to the electrolyte and at temperatures of treatment of 60, 70, 80, 90 and 100° C., respectively. The amount of Ce (IV) and the other products of reaction were measured as a function of the time at the different temperatures of treatment and the results are reported in FIGS. 7 to 10.

An analysis of the obtained results shows that a temperature of 100° C. and a time of minutes are sufficient to achieve the desired purification. In fact, after about minutes, there was no modification in the amount of organic products in the solution. The only product that required a longer time of treatment is toluic acid. Precautionary measures led to the selection of a time of minutes. However, it is worth noting that temperatures higher than 100° C. were not studied because they are very close to the boiling temperature of the electrolyte. Treatment in a tank under pressure can be designed to reach higher temperatures. However, since the differences observed between the temperatures of 90 and 100° C. were small, such a treatment is probably not necessary in view of the small increases in temperature (ex: 110° C.).

At 60° C., the oxidation of toluic acid to terephtalic acid (FIG. 10) does not seem to be completed in the chosen time interval. In fact, the concentration increases in the solution during the studied time interval, whereas at temperatures higher than 70° C., a decrease in the concentration was observed.

For the treatment of the electrolyte used for the electrosynthesis of p-tolualdehyde, the following parameters were used: an addition of 10% (v/v) of a regenerated cerium solution with a concentration of 0,4 M of Ce IV, a treatment temperature of 100° C. and a treatment time of 30 minutes. Obviously, the treatment time must be optimized again when used on a large scale. Indeed, this time should depend at least in part on the mixing conditions and the geometry of the reactor.

Figure 11:
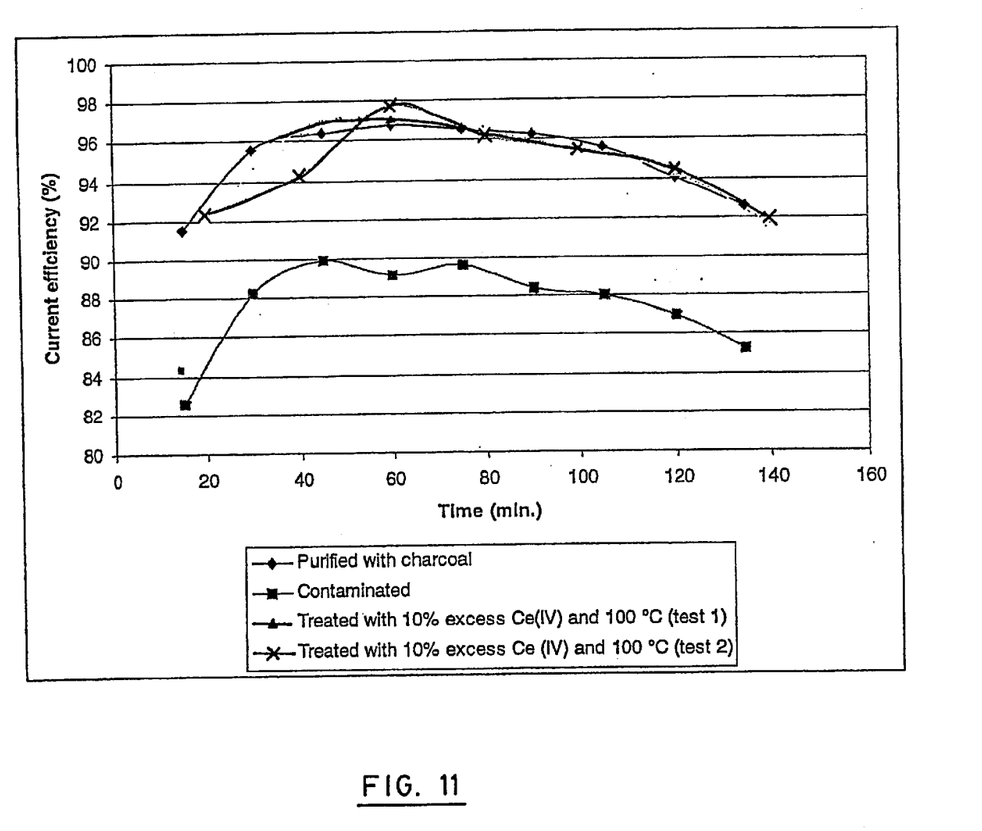
FIG. 11 is a graph showing the current efficiency of four solutions, viz one that is purified with charcoal, another one that is contaminated and two others that underwent a similar thermal treatment for minutes at 100° C. with an addition of 10% of Ce IV.

FIG. 11 shows that the selection of parameters was very well done and that the current efficiency of the used solution after treatment was as good as that of a clean solution. FIG. 11 also shows that the reproducibility is excellent since the results obtained for the two treated solutions are almost identical.

EXAMPLE 2

Electrosynthesis of Azelaic and Pelargonic Acids with Cr III/CrVI

The electrolyte used to mediate the oxidation of oleic acid in order to synthesize pelargonic and azelaic acids is the Redox couple Cr III/Cr VI. A combination of Ce III/Ce IV and Cr III/Cr VI can also be used to mediate the oxidation of oleic acid. However, an electrolyte made up only of cerium will not work.

Untreated Electrolyte (Prior Art) With a <<new>> chromium solution used as a reference with no organic matter contained therein, a current efficiency of 78% with 0,22 M of Cr VI was obtained.

With the same solution after having been used once and not having undergone any treatment other than extraction, filtration and decantation (hereafter called <<used untreated solution>>), the current efficiency dropped tremendously in comparison to the new solution. For the used untreated solution there was a drop in current efficiency of 40% during regeneration of the electrolyte, the efficiency was 48% at 0,20 M of Cr VI.

However, it was observed that by letting the used untreated solution rest for 2 days, there was a higher current efficiency, 62% with 0.227 M of Cr VI. It seems that by letting the electrolyte rest for a certain period of time, the current efficiency would increase during the regeneration. This increase in efficiency can be explained by the fact the residual Cr VI in the solution oxidizes the organic molecules contained therein even at room temperature. A decrease in the Cr VI concentration determined by titration, after letting the electrolyte rest for a certain period of time, has confirmed such hypothesis of an oxidation. This oxidation can be combined with the evaporation of some organic products dissolved in the electrolyte, like, for example, the extraction solvent (petroleum ether).

Treatment by Extraction with Valeric Acid

Valeric acid is a five carbon atoms organic acid. The degradation products in the solution mostly consist of shorter chain acids and should have an affinity for valeric acid. By using valeric acid as extraction solvent after the oxidation reaction, two extractions were carried out on the electrolyte with 100 ml of valeric acid. Then, a second series of extractions were performed with two portions of 100 ml of petroleum ether at 35–60° C. to remove the traces of valeric acid in the electrolyte.

With this treatment, the total amount of organic carbon (TOC.) was reduced from 3,95 g/l in the untreated electrolyte to 2,031 g/l in the electrolyte treated with valeric acid.

To determine the true efficiency of such a treatment, a regeneration of the electrolyte was carried out. A current efficiency of 45% was obtained with 0,1640 M of Cr VI.

This was clearly insufficient for use with electrolysis processes.

Treatment with Pelargonic Acid

With the same basic premise in mind as for the treatment with valeric acid, extractions were carried out on the electrolyte with two batches of 100 ml of pelargonic acid. These extractions were followed by other extractions with two batches of 100 ml of petroleum ether at 35–60° C. The TOC. obtained was of 2,261 g/l as compared to 3,95 g/mi of the untreated electrolyte. The current efficiency of 48% was obtained with 0,20 M of Cr VI.

This treatment is clearly not efficient enough to justify its use.

Thermal Treatment (Invention) By heating the used untreated solution, it was discovered that the oxidation process could be accelerated when the solution was allowed to rest for 2 hours. After the reaction was completed, the electrolyte was heated and kept at 110° C. for 90 minutes. The above-mentioned time does not include the time it took for the solution to reach 110° C. In doing so, oxidation with the residual Cr VI was favored up to the decomposition of the products into $CO_2$, and the solvent and some organic compounds were eliminated by evaporation. Thermal treatment gave the largest decrease in TOC. After this treatment, there was only 1,67 gel of TOC. Such corresponds to a decrease in 64% TOC. The current efficiency of the regeneration was approximately 78% for a solution with 0,21 M of Cr VI, as compared to the current efficiency of 78% for a <<new>> solution. Heating is therefore important for the treatment of the electrolyte.

Table 3 summarizes the data obtained during the determination of the treatment to be used.

TABLE 3

Current efficiency obtained with the different treatments of the electrolyte

| Trial | Type of Treatment | Peak Concentration of Cr VI (M) during electrolysis | Cumulative current efficiency (%) |
|---|---|---|---|
| E-02 (new solution) | Reference | 0.2207 | 79.36 |
| E-03 (new solution) | Reference | 0.2227 | 77.19 |
| E-04 (new solution) | Reference | 0.1770 | 89.12 |
| E-06 (used untreated) | Reaction | 0.2146 | 44.89 |

TABLE 3-continued

Current efficiency obtained with the different treatments of the electrolyte

| Trial | Type of Treatment | Peak Concentration of Cr VI (M) during electrolysis | Cumulative current efficiency (%) |
|---|---|---|---|
| E-07 (used untreated) | Reaction | 0.2437 | 50.72 |
| E-09 (used untreated) | Reaction | 0.2023 | 53.43 |
| E-10 | Heating | 0.2210 | 78.06 |
| E-12 | Reaction | 0.2307 | 41.05 |
| E-13 | Heating | 0.2780 | 87.20 |
| E-14 | Pelargonic | 0.2026 | 47.65 |
| E-15 | Pelargonic | 0.2267 | 62.02 |
| E-17 | Heating | 0.2493 | 37.81 |
| E-18 | Reference | 0.2666 | 65.57 |
| E-19 | Valeric | 0.1680 | 39.51 |
| E-20 | Valeric | 0.1600 | 49.54 |
| E-21 | Reaction | 0.2140 | 44.70 |
| E-22 | Reaction | 0.1933 | 40.17 |
| E-25 | Heating | 0.2093 | 73.52 |
| E-32 | Heating | 0.2653 | 66.89 |

Tests were also carried out with a FM01 cell. The reference solution used in this cell had a current efficiency of 66% with 0,267 M of Cr(VI). The solution that was used for the chemical reaction and was treated by heating, had a current efficiency of 67% with 0,265 M of Cr(VI). Thermal treatment is therefore very efficient.

Table 4 summarizes the results obtained with the different methods of treating an electrolytic solution.

TABLE 4

| Treatment | Total organic carbon concentration (g/l) |
|---|---|
| Untreated | 3,965 |
| Extraction with valeric acid | 2,031 |
| Extraction with pelargonic acid | 2,261 |
| Cooling and fine filtration | 3,550 |
| Activated charcoal | 3,503 |
| Heating | 1,674 |

Optimization of the Treatment

An optimization of the treatment was done with the two variables that had to be optimized, viz. time and temperature. Time and temperature are two factors that are linked together. Therefore, the "surface response" software ECHIP was used to check their interaction. Another parameter to be optimized is the minimum Cr VI concentration necessary in the solution to be heated in order to considerably decrease the level of TOC in the electrolyte.

With ECHIP, an experimental testing plan was put forward. To perform this testing plan, oxidation of oleic acid was first carried out. Then, the electrolyte was divided into several 20 ml portions and a test was carried out on every one of these portions. The anlysis of Cr VI allows to track the progression of the oxidation of the impurities. The result that were reported show that the higher are the temperature and the time, the higher is the degree of progression of the oxidation. The results also show that temperture is the parameter which influences the treatment the most.

Table gives an overview of the tests carried out during the experimental testing proposed by the ECHIP software.

TABLE 5

Treatments suggested by ECHIP and results obtained during system optimization

| Trial | Time (min) | Temperature (° C.) | Cr(VI) (M) |
|---|---|---|---|
| 4 | 75,0 | 120,0 | 0,0087 |
| 11 | 28,3 | 93,3 | 0,1820 |
| 5 | 75,0 | 40,0 | 0,2047 |
| 2 | 5,0 | 80,0 | 0,1853 |
| 10 | 75,0 | 93,3 | 0,0900 |
| 2 | 5,0 | 80,0 | 0,1820 |
| 5 | 75,0 | 40,0 | 0,2280 |
| 8 | 28,3 | 40,0 | 0,1733 |
| 3 | 40,0 | 120,0 | 0,0080 |
| 1 | 5,0 | 120,0 | 0,573 |
| 3 | 40,0 | 120,0 | 0,0027 |
| 7 | 51,7 | 40,0 | 0,2040 |
| 6 | 5,0 | 40,0 | 0,2400 |
| 1 | 5,0 | 120,0 | 0,0780 |
| 4 | 75,0 | 120,0 | 0,0020 |
| 9 | 75,0 | 66,7 | 0,1240 |
| 12 | 70,0 | 60,0 | 0,1407 |
| 13 | 20,0 | 60,0 | 0,1800 |
| 14 | 20,0 | 90,0 | 0,1567 |
| 15 | 70,0 | 90,0 | 0,0607 |

Cr VI Concentration (Inferior Limit)

Tests were carried out in order to evaluate the impact of a higher concentration of Cr VI on the efficiency of the regeneration current and also to evaluate the minimal amount of Cr VI that the solution must contain to have a good current efficiency after treatment.

In order to determine the influence of the Cr VI concentration on the quality of the treatment (TOC level and regeneration current efficiency), different amounts of a 0,6 M Cr VI solution were added to a starting solution containing 0,2 M of Cr VI, in order to increase the level of the Cr VI concentration. Subsequently, the solution was heated at 120° C. for 90 minutes.

The obtained results show that the level of TOC. decreases when the Cr VI concentration in the solution increases. However, it is important to note that in order to have a 0,25 M concentration, it was necessary to add 3,58 ml of a 0,6 M solution to the 20 ml sample of 0,2 M. Such corresponds to 20% of the volume of the initial solution. Regeneration of this solution was carried out and the current efficiency was increased by approximately 2% only.

Table 6 summarizes the obtained results.

TABLE 6

TOC concentration in the electrolyte as a function of the Cr VI concentration

| Sample | Volume of added solution (ml) | Concentration of Cr VI | TOC of the electrolyte (g/l) |
|---|---|---|---|
| Start (ref.)-20 ml | 0,00 | 0,1907 | 1,990 |
| 1 | 3,58 | 0,2500 | 0,845 |
| 2 | 10,14 | 0,3400 | 0,195 |
| 3 | 16,69 | 0,3800 | 0,213 |

The above study of different treatments for the oxidative acid solution, has permitted to optimize the treatment. To have an efficient regeneration of the solution, heating of the same in the presence of Cr VI is important. Heating in the presence of Cr VI permits to oxidize a portion of the organic compounds that are present in the solution and to evaporate volatile molecules, particularly the extraction solvent. Therefore, the current efficiency was found to increase to a value of about 80%. This value is very close to the maximum current efficiency (82%) obtained with a new solution. Optimization of the treatment by the ECHIP software has permitted to assert that a maximum amount of impurities is oxidized when heating is performed as long as possible at a high temperature (110° C.). It also showed that the temperature plays a more prominent role than the duration of treatment.

In summary, regeneration by thermal treatment of the electrolyte constitutes a key feature of the method according to the invention. Because of the nature of the products to be removed, the regeneration step was far from being obvious. In fact, carboxylic acids and diacids have a very high affinity for the aqueous oxidative phase. Moreover, solvents capable of extracting these compounds while remaining stable chemically and electrochemically in the medium, are practically non-existent.

EXAMPLE 3

Electrolytic Regeneration of a Ce IV Solution for the Electrosynthesis of Chlorobenzoquinone The electrolyte used to catalyze the oxidation of chloroaniline to chlorobenzoquinone is the Redox couple Ce III/Ce IV.

This series of experiments was carried out in order to determine which one of the known treatments would be the best one for the purification of the electrolyte before its regeneration in the electrolysis cell. The three treatments selected for the purpose of comparison were the following: an addition of an excess of Ce IV to the electrolyte before regeneration, the use of a more efficient solvent during the extraction step, and an improvement in the filtration step.
Addition of an Excess of Ce IV to the Electrolyte Before Regeneration The idea behind using this treatment is to have a current efficiency differential similar to that of a non-used solution at the beginning of the regeneration of the solution in the electrolysis cell.

200 ml of a solution containing 0,424 M Ce IV and 3,5 M methanesulfonic acid (84,8 mmoles of Ce IV), and 140 ml of a 1M solution of Ce III were added to 1160 ml of used electrolyte solution. The total volume of the resulting mixture was 1500 ml. The mixture was then heated at 60° C. for minutes. Then the solution was regenerated in the electrolysis cell.

The current efficiency at the beginning of the regeneration was 83% for the solution with a Ce IV addition. This result is very similar to what is obtained for an unused solution, which is approximately 82%. The current efficiency values remained similar as the regeneration took place, that is, the Ce III concentration decreased and the Ce IV concentration increased.
Use of a More Efficient Solvent During the Extraction Step This test has permitted to determine whether the impurities that were present in the solution were in a dissolved or insoluble state.

1250 ml of the used electrolyte solution were extracted in five consecutive steps by using 250 ml of dichloroethane (for a total of 1250 ml of dichloroethane) at 60° C. After the phase separation, the electrolyte was regenerated electrochemically.

The differential current efficiency for this treatment was 67%. This is an improvement over the current efficiency of an untreated solution, which was 59% only. This increase in the current efficiency shows that some of the impurities which affect the current efficiency are in a dissolved state. However, the current efficiency resulting from the treatment is not sufficiently high to compare it advantageously to the results obtained with a Ce IV addition. Thus, a treatment using a more efficient solvent does not represent an improvement substantial enough to justify its use.

Filtration Step

This other test has permitted to confirm the results obtained during the extraction step by using a more efficient solvent. If the impurities which decrease the current efficiency were in an insoluble state after the treatment, there should have been a substantial improvement in the current efficiency in the electrolysis cell. If they were present in a dissolved state, the treatment should not affect the current efficiency in the electrolysis cell.

As soon as the electrolysis solution was cooled down to room temperature, it was subjected to a first filtration under vacuum using a Whatman® 934-AH glass fiber filter of 1,5 microns, and then a second filtration with glass fiber filter of 1 micron. The solution was then transfered to the electrolytic cell for its regeneration.

The filtration step of the electrolytic solution had no impact on the current efficiency since the starting current efficiency for the filtered solution was of 58%, while the starting current efficiency for an untreated solution was of 59%. This confirms the results of the extraction treatment made with dichloroethane, which indicated that the impurities were present in a dissolved state.

Thus, in this example, three treatments were studied to determine which one would be the most efficient one to increase the current efficiency of a used electrolytic solution. The most efficient treatment was the one which involved an addition of Ce IV in the electrolytic solution. This treatment has allowed to obtain an initial current efficiency equal to the one of an unused solution. This treament consisted in adding, in this case, an equivalent of 15% of the initial electrolyte volume. This treatment seems relatively rapid since, at 60° C., 98% of the Ce IV that was added, was consumed in 30 minutes.

What is claimed is:

1. A method for purifying a Redox mediator used in a chemical process of oxidation of organic compounds before said mediator is regenerated in an electrolysis cell, comprising:

recovering the mediator in the form of a solution containing volatile, soluble and insoluble impurities;

subjecting the solution containing the mediator to a thermal treatment, said treatment being carried out in a reactor that is maintained at a temperature that is high enough to allow oxidation of the impurities by means of the left-over unused catalyst present in the solution and to simultaneously allow elimination of the volatile impurities present in the solution; and filtering the solution that contains the mediator to remove the insoluble impurities therefrom.

2. Method according to claim 1, further comprising:

adding to the reactor a given amount of the mediator regenerated in the electrolysis cell in order to increase the amount of said unused mediator present in the solution and therefore to complete oxidation of the impurities.

3. Method according to claim 1, wherein the thermal treatment is carried out at a temperature ranging between 40 and 120° C.

4. Method according to claim 3, wherein the thermal treatment is carried out at a temperature ranging between 70 and 110° C.

5. Method according to claim 4, wherein the thermal treatment is carried out at a temperature ranging between 90 and 100° C.

6. Method according to claim 5, wherein the Redox mediator is selected from the group consisting of Cr III/Cr VI, Ce III/Ce IV and mixtures thereof.

7. Method according to claim 6, wherein the chemical process of oxidation is a process synthesis of p-tolualdehyde from p-xylene.

8. Method according to claim 6, wherein the chemical process of oxidation is a process synthesis of naphtoquinone or its derivatives from naphtalene or its derivatives.

9. Method according to claim 6, wherein the chemical process of oxidation is a process synthesis of azelaic acid and pelargonic acid from oleic acid.

10. Method according to claim 5, comprising:

adding to the reactor a given amount of the mediator regenerated in the electrolysis cell in order to increase the amount of the said unused mediator present in the solution and therefore to complete the oxidation of the impurities.

11. Method according to claim 10, wherein the Redox mediator is selected from the group consisting of Cr III/Cr VI, Ce III/Ce IV and mixtures thereof.

12. Method according to claim 11, wherein the chemical process of oxidation is a process synthesis of p-tolualdehyde from p-xylene.

13. Method according to claim 11, wherein the chemical process of oxidation is a process synthesis of naphtoquinone or its derivatives from naphtalene or its derivatives.

14. Method according to claim 11, wherein the chemical process of oxidation is a process synthesis of chlorobenzoquinone from chloraniline.

15. Method according to claim 11, wherein the chemical process of oxidation is a process synthesis of azelaic acid and pelargonic acid from oleic acid.

16. Method according to claim 1, wherein the Redox mediator is selected from the group consisting of Cr III/Cr VI, Ce III/Ce IV and mixtures thereof.

17. Method according to claim 1, wherein the chemical process of oxidation is a process synthesis of p-tolualdehyde from p-xylene.

18. Method according to claim 1, wherein the chemical process of oxidation is a process synthesis of naphtoquinone or its derivatives from naphtalene or its derivatives.

19. Method according to claim 1, wherein the chemical process of oxidation is a process synthesis of chlorobenzoquinone from chloraniline.

20. Method according to claim 1, wherein the chemical process of oxidation is a process synthesis of azelaic acid and pelargonic acid from oleic acid.

\* \* \* \* \*